United States Patent
Prager et al.

(10) Patent No.: US 8,967,810 B1
(45) Date of Patent: Mar. 3, 2015

(54) METHODOLOGY TO IDENTIFY THE SCLERAL SPUR

(71) Applicants: Thomas C. Prager, Spicewood, TX (US); Thomas A. Burba, Plymouth, MN (US); David R. Hardten, Excelsior, MN (US)

(72) Inventors: Thomas C. Prager, Spicewood, TX (US); Thomas A. Burba, Plymouth, MN (US); David R. Hardten, Excelsior, MN (US)

( * ) Notice: Subject to any disclaimer, the term of this patent is extended or adjusted under 35 U.S.C. 154(b) by 16 days.

(21) Appl. No.: 13/987,615

(22) Filed: Aug. 13, 2013

(51) Int. Cl.
*A61B 3/00* (2006.01)
*A61B 3/14* (2006.01)
*A61B 3/117* (2006.01)

(52) U.S. Cl.
CPC ........................................ *A61B 3/117* (2013.01)
USPC .......................................... 351/246; 351/206

(58) Field of Classification Search
CPC .... A61B 3/0033; A61B 3/1005; A61B 3/117; A61B 3/14
USPC .......................................................... 351/206
See application file for complete search history.

(56) References Cited

U.S. PATENT DOCUMENTS

| | | | |
|---|---|---|---|
| 6,942,343 B2 * | 9/2005 | Farberov | 351/219 |
| 2010/0106073 A1 * | 4/2010 | Haffner et al. | 604/8 |
| 2012/0140174 A1 * | 6/2012 | Hee et al. | 351/206 |

* cited by examiner

*Primary Examiner* — Jordan Schwartz
(74) *Attorney, Agent, or Firm* — Law Offices of Steven W. Weinrieb

(57) ABSTRACT

A method of determining the location of the scleral spur, to allow measurements of the anterior chamber of the eye to facilitate diagnosis or treatment of the eye. The method utilizes ultrasonic biomicroscopy apparatus to image the anterior chamber and several millimeters of sclera and align indicators, or along the scleral-uveal interface and the corneal-aqueous interface. These indicators can be lines, dots or any shape or colors. The intersection of these indicators is used as an estimated location of the scleral spur for measuring anterior chamber angle, angle opening distance, or other aspects of the eye. The disclosure includes methods of locating the scleral spur, software for locating the scleral spur using computerized imaging apparatus, and systems including computerized imaging apparatus and software for locating the scleral spur.

10 Claims, 12 Drawing Sheets

METHODOLOGY TO IDENTIFY THE SCLERAL SPUR

CROSS REFERENCES TO RELATED APPLICATIONS

This patent application claims benefit from the earlier filed U.S. Provisional Application No. 61/854,726 filed Apr. 30, 2013, entitled "Ultrasonic Biomicroscopy (UBM) Methodology to Identify the Scleral Spur", and is hereby incorporated into this application by reference as if fully set forth herein.

BACKGROUND OF THE INVENTION

1. Field of the Invention

The present invention pertains to ophthalmic diagnosis and therapy, and more particularly, its apparatus, software, means, and methods for diagnosing and treating diseases of the eye. In particular, the present invention provides for improved evaluation of anterior chamber angle by accurately and repeatedly identifying the location of the scleral spur.

The scleral spur is a subtle ridge of the sclera at the level of the limbus interposed between the posterior portion of Schlemm's canal and the anterior part of the ciliary body. The scleral spur is the structure to which some of the ciliary muscle fibers are attached. On cross section, it appears as a hook-like process deep to the scleral venous sinus; relatively rigid, it provides attachment for the meridional fibers of the ciliary body.

Most importantly, this subtle protrusion of the sclera into the anterior chamber is the origin of the longitudinal fibers of the ciliary muscle and is attached anteriorly to the trabecular meshwork. Accurately determining the location of the scleral spur is required in order to determine whether the anterior chamber angle is open, narrow or closed in a particular glaucoma patient. Other established measurements such as angle opening distance and trabecular-iris space area necessitate first identifying the spur.

Thus, the scleral spur is considered the gateway to the anterior chamber and its identification is required for determining whether the anterior chamber angle is open, narrow or closed. The anterior chamber angle, and whether it is open, narrow or closed, is important in determining if any or which medical or surgical interventions should be initiated in a particular patient.

2. Description of the Prior Art

Angle closure glaucoma is a leading cause of blindness, and it is potentially preventable if diagnosed early, before irreversible damage has occurred to the optic nerve.

The current standard for the assessment of anterior chamber angle status is dark-room gonioscopy, in which anterior chamber (iridocorneal) angle is directly visualized. While there is a standardized method of examining, this technique is subjective and a skill that requires that a trained eye specialist identify subtle anatomical structures after placing a lens on the eye while the patient sits in front of a slitlamp, a type of horizontal microscope.

The best way to quantitatively measure the anterior chamber angles and other key parameters is by using anterior chamber imaging approaches such as optical coherence tomography (OCT) or ultrasound biomicroscopy (UBM). Both existing imaging approaches, however, also have shortcomings. OCT is a newer technology which is promising, but cannot effectively image deeper ocular structures. Therefore, the regions behind the iris are not visible to the eye care specialist. UBM allows visualization behind the iris and is useful, but locating the scleral spur is difficult, requiring significant training and experience.

Accurately locating the subtle scleral spur structure with even the highest frequency ultrasound equipment is often difficult and as a consequence the location of the spur must often be estimated.

SUMMARY OF THE INVENTION

The general purpose of the present invention is to provide means to identify the scleral spur to facilitate diagnosis or therapy of the eye.

According to one embodiment of the present invention, there is provided a method for identifying the scleral spur.

According to another embodiment of the present invention, there is provided means for identifying the scleral spur.

According to yet another embodiment of the present invention, there is provided a system for identifying the scleral spur.

A method of identifying the scleral spur includes steps of: providing ultrasonic biomicroscopy apparatus with adjustable gain, optional tissue differentiation by colorization and indicator with measurement functions, adjustable gain to facilitate visualization of the scleral/uveal tissue interface. The first step is placing an indicator such as the first indicator being linear or any shaped graphical on the scleral/uveal tissue interface, then placing a second curvilinear indicator on the inner corneal surface, locating the intersection of the first indicator and second curvilinear indicator, and using this intersection as the location of the scleral spur for measurements prior to diagnosis of the eye.

Means for identifying the scleral spur, for use with ultrasonic biomicroscopy apparatus, includes the functions of: adjusting the display to facilitate visualization of the scleral/uveal tissue interface which typically requires an area several millimeters from the adjacent limbus, to allow creation of a first indicator on the display aligned with the scleral/uveal tissue interface. Next is the creation of a second curvilinear indicator on the display aligned with the inner corneal surface. Finally, the intersection of the first indicator and second curvilinear indicator is the estimated location of the scleral spur from which the geometric status of the anterior chamber angle can be determined.

A system for identifying the scleral spur, including computerized imaging apparatus and means for image processing, the computerized imaging apparatus having a display and user interface elements and means of adjusting the contrast, brightness, or color of the eye segments on the display as well as the means for image processing including the functions of actuating adjustment of the display to facilitate visualization of the scleral/uveal tissue interface, creating a display of the first indicator aligned with the scleral/uveal tissue interface, creating a second curvilinear indicator on the display aligned with the inner corneal surface, locating the intersection of the first indicator and second curvilinear indicator, and assessing the geometry of the anterior chamber angle using this intersection as the location of the scleral spur.

One significant aspect and feature of the present invention is enhancing ultrasonic biomicroscopy to better locate the scleral spur to aid in the diagnosis and subsequent ocular treatment options.

Another significant aspect and feature of the present invention is facilitated location of the scleral-uveal interface, corneal curvature, and intersection point.

Yet another significant aspect and feature of the present invention is automating at least part of the evaluation of the anterior chamber angle of the eye.

Having thus briefly described embodiments of the present invention, and having mentioned some significant aspects and features of the present invention, it is the principal object of the present invention to provide an improved examination of the eye.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
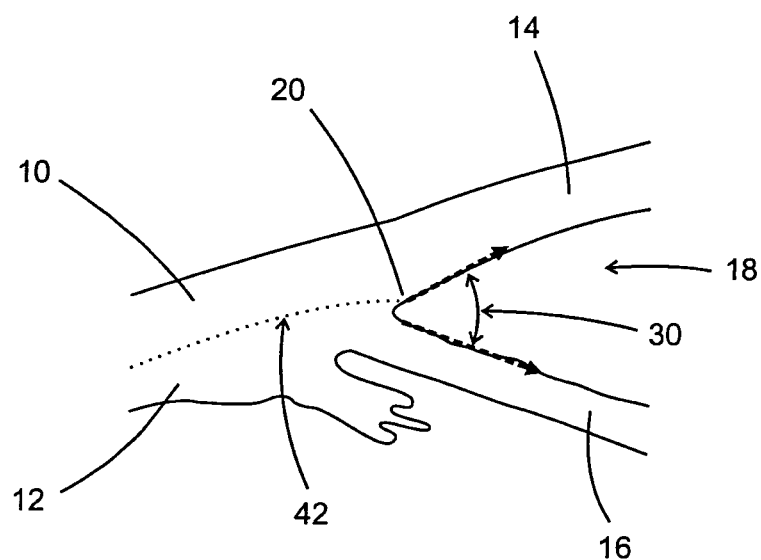
FIG. 1 illustrates key anatomical landmarks and measurements for examination of the anterior chamber of the eye.

FIG. 1 illustrates key anatomical landmarks and measurements for examination of the anterior chamber of the eye. Shown are the locations of scleral tissue 10, uveal tissue 12, the scleral-uveal interface 42, the cornea 14, the iris 16, aqueous humor 18, the scleral spur 20, and the anterior chamber angle 30 is indicated. Anterior chamber angle 30 can be particularly useful in assessing the eye and diagnosing specific disease states or disorders, such as distinguishing between open-angle glaucoma, narrow-angle and closed-angle glaucoma. This distinction can be important in determining the appropriate course of any required therapy. Accurately determining the location of the scleral spur is important for proper evaluation of anterior chamber geometry. A proper evaluation of anterior chamber angles requires the location of scleral spur 20 to be known. The image requirements to identify the scleral spur:

- obtain image of the anterior chamber including the cornea and iris,
- obtain image representing several millimeters of scleral and uveal tissue adjacent to the anterior chamber;
- obtain image combining both anterior chamber and scleral/uveal tissue.

The current standard for diagnosing anterior chamber angles is dark-room gonioscopy, in which the angle and fluid outflow can be visually assessed by an eye care specialist. However, this procedure is also subjective, and a quantitative image evaluation such as using ultrasound biomicroscopy is often preferred. For such a quantitative evaluation to be useful, an accurate location of the scleral spur is required. Measurements of the angle geometry are important in diagnosing open-angle glaucoma, narrow-angle glaucoma, closed-angle glaucoma, and other problems of the eye.

Figure 2:
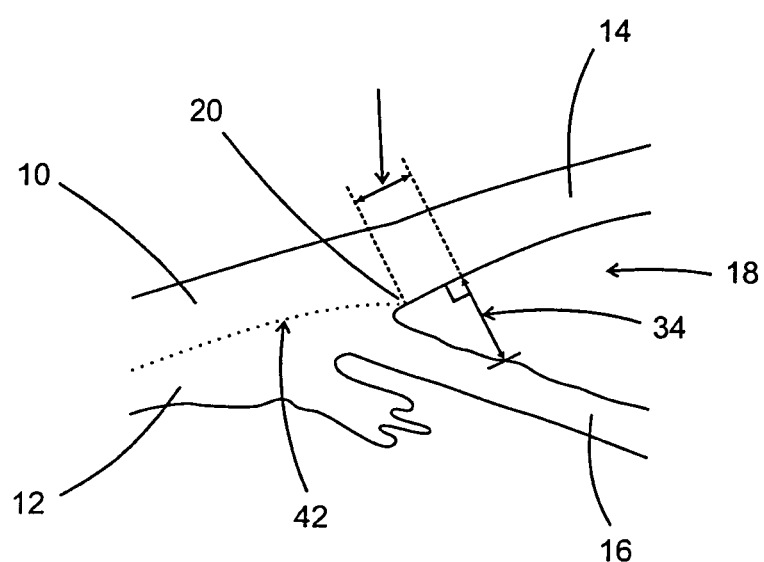
FIG. 2 illustrates key anatomical landmarks and measurements for examination of the angle opening distance.

FIG. 2 illustrates key anatomical landmarks and measurements similar to FIG. 1, but illustrating the measurement of angle opening distance 34. Angle opening distance 34 is measured at an angle measurement distance 32 from scleral spur 20. Angle measurement distance is typically 500 or 750 micrometers from the scleral spur, but other distances can be used. Angle opening distance is the distance from the surface of cornea 14 to the surface of iris 16, measured perpendicular to the surface of cornea 14 frequently at 500 micrometers from the scleral spur. Therefore, a proper determination of angle opening distance 34 requires the location of scleral spur 20 to be known.

Figure 3:
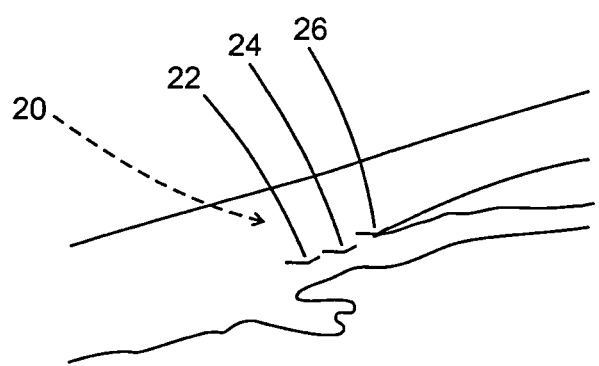
FIG. 3 illustrates possible locations of the scleral spur.

FIG. 3 illustrates key anatomical landmarks and measurements similar to FIGS. 1 and 2, but illustrates possible locations 22, 24, and 26 of scleral spur 20. The actual location of scleral spur 20 can be difficult or impossible to determine based on standard clinical evaluation tools. Thus, the actual location of scleral spur may be incorrectly estimated, such as at location 26 when in reality it is at location 22, and so forth. Since scleral spur 20 is used as a starting point for various clinically important measurements, such possible inaccuracies can lead to inadequate diagnosis and potentially to suboptimal clinical therapy decisions.

Figure 4:
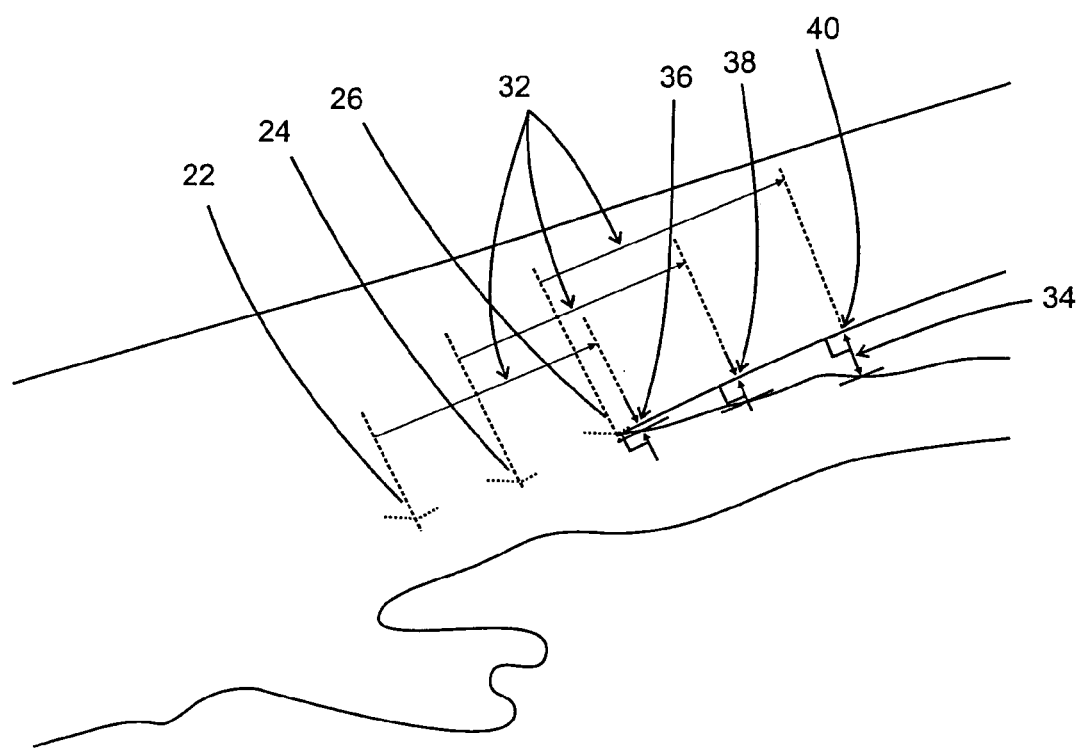
FIG. 4 illustrates uncertainties in measuring the angle opening distance.

FIG. 4 illustrates the problem that can arise when the location of scleral spur 20 is not accurately known. If the scleral spur location is not known, and could be at location 22, 24, or 26, for example, then when the angle opening distance 34 is measured at position 36, 38, or 40, a large variation in angle opening distance 34 can be obtained, with potentially large error. This error can again lead to inadequate diagnosis and potentially to suboptimal clinical therapy decisions.

Figure 5:
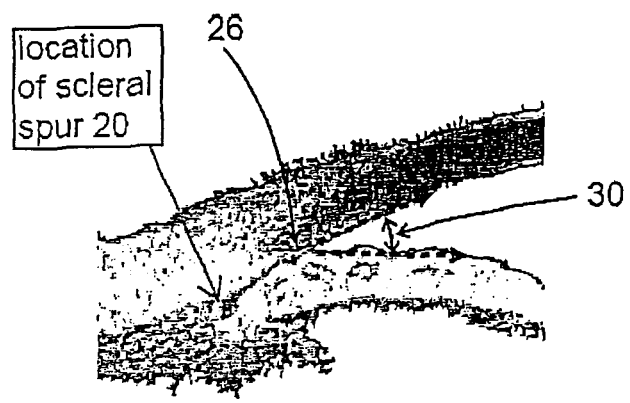
FIG. 5 illustrates an ultrasonic biomicroscopy image and one estimated scleral spur location and the resulting status of measured anterior chamber angle.

FIG. 5 illustrates an ultrasound biomicroscopy image, in which the scleral spur 20 is not visible, so a definitive answer of whether the angle being open, narrow or closed may not be possible. In this example of a closed angle, the scleral spur 20 is not at location 26 where the iris is in contact with the inner cornea, but rather several mm distal at spur 20, and the angle geometry should be measured using that location 20 as a starting point.

Figure 6:
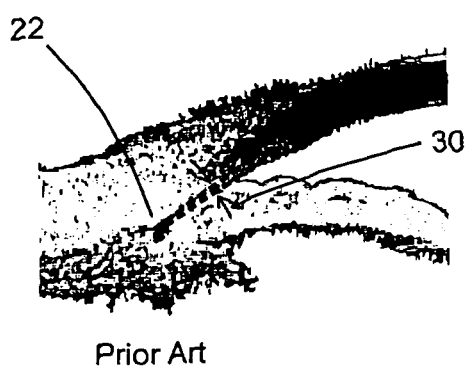
FIG. 6 illustrates the ultrasonic biomicroscopy image of FIG. 5 but with a different estimated scleral spur location and a different resulting measured anterior chamber angle.

FIG. 6 illustrates the same ultrasound biomicroscopy image as in FIG. 5, in which the scleral spur 20 is again not visible. In this example, the scleral spur 20 is inaccurately located at point 22, and the angle geometry would be measured using that incorrect location as a starting point. Both locations 22 and 26 as well as other locations, appear reasonable given the limited ability to visualize scleral spur 20, but they lead to very different angle geometry measurements, and potentially to different diagnostic interpretations and different therapy decisions.

Figure 7:
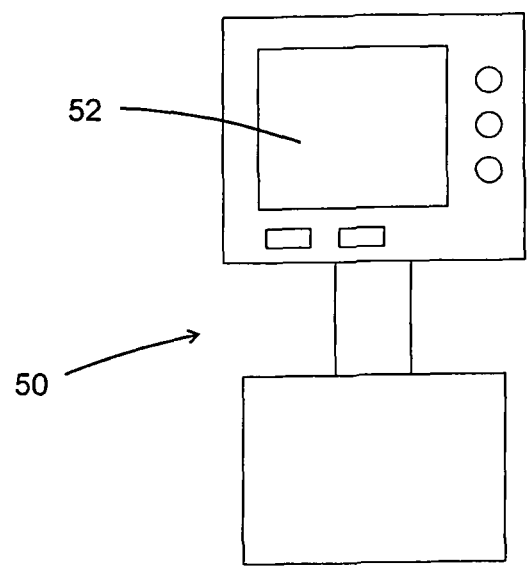
FIG. 7 illustrates computerized imaging apparatus.
Figure 8:
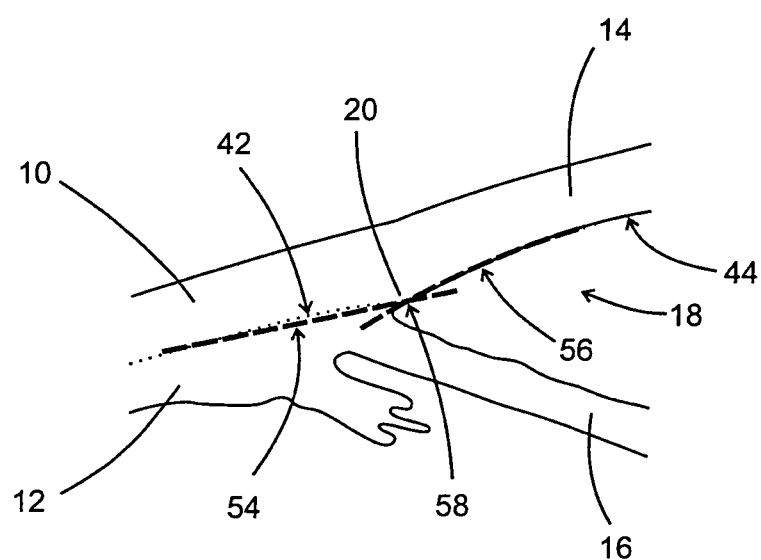
FIG. 8 illustrates embodiments of the present invention in locating the scleral spur.

FIGS. 7 and 8 illustrate the present invention for estimating the scleral spur location.

FIG. 7 illustrates computerized imaging apparatus 50, capable of gain, contrast and color adjustment and with indicator and measurement functions. Computerized imaging apparatus 50 can comprise ultrasonic biomicroscopy apparatus, optical coherence tomography, etc. Computerized imaging apparatus 50 includes display 52 which can be used to visualize images of the eye as well as facilitating anatomical measurements of the eye. Computerized image processing can be performed real-time during an imaging examination, or images recorded during an examination can be analyzed later, but still using the present approach. Additional and/or separate computing apparatus can be utilized for some or all of the analysis.

Embodiments of the present invention are schematically illustrated on FIG. 8. The eye anatomy is examined using computerized imaging apparatus 50. First, computerized imaging apparatus 50 is used to display an image of the anterior chamber of the eye on display 52, and the gain, display, contrast or coloration is adjusted to distinguish scleral-uveal interface as differing tissue reflectivity will allow separation of scleral from uveal tissue 42. A first indicator 54 is created and aligned onto scleral-uveal interface 42 as shown. First indicator 54 is usually a straight line which matches the relevant portion of scleral-uveal interface 42. Alternatively, first indicator 54 can be a circular arc or other curve which matches the scleral-uveal interface 42. First indicator 54 can be created and/or adjusted manually, or an automated function can be used to enhance the accuracy of discerning the scleral-uveal interface 42. Computerized imaging apparatus 50 may have a measurement caliper or similar function which can be used or modified for use in creating a straight line aligned with scleral-uveal interface 42.

Optionally, the gain, display contrast or coloration can be adjusted to distinguish the inner or endothelial surface of cornea 44 and allow corneal-aqueous interface to be visualized. A second curvilinear indicator 56 is created and aligned onto the corneal-aqueous interface 44 as shown. The first indicator 54 and second curvilinear indicator 56 are manually or automatically extended if necessary until they intersect with each other at intersection point 58 which may be graphically indicated with an arrow and optional removal of the two indicators. Intersection point 58 is used as the estimated location of scleral spur 20, even if scleral spur 20 cannot be visualized on the display of the computerized imaging apparatus. In the example of FIG. 8, first indicator 54 is illustrated as a dashed straight line, and second curvilinear indicator 56 is illustrated as a dashed circular arc. However, other line and curve shapes can be utilized. Further, automatic image processing can be used to automatically detect contrast differences or other graphical elements to create one indicator or both indicators 54 and 56.

In one approach, second curvilinear indicator 56 is created by placing at least 3 or more dots along corneal-aqueous interface 44 and creating an arc, the second curvilinear indicator 56. The second curvilinear indicator 56 is extrapolated to intersect the previously obtained first indicator 54. In another method, a software contrast detection device can automatically pick out the line of demarcation between cornea 14 and aqueous humor 18 at corneal-aqueous interface 44. Various image processing tools, combination of rough manual location and automatic refinement, or other manual and/or automatic software tools can be utilized to create second curvilinear indicator 56. Similar approaches can be utilized to create first indicator 54, if desired.

Once the estimated location of scleral spur 20 is determined by location of intersection point 58, this location is used for measurement of anterior chamber angle 30, angle opening distance 34, or other evaluations and measurements. Various automatic or manual graphical and image processing methods and devices can be utilized for these other evaluations and measurements, which can be performed using the location of the scleral spur 20 as determined by the present invention. Graphical indicators can be provided to facilitate diagnosis of the eye.

Figure 9:
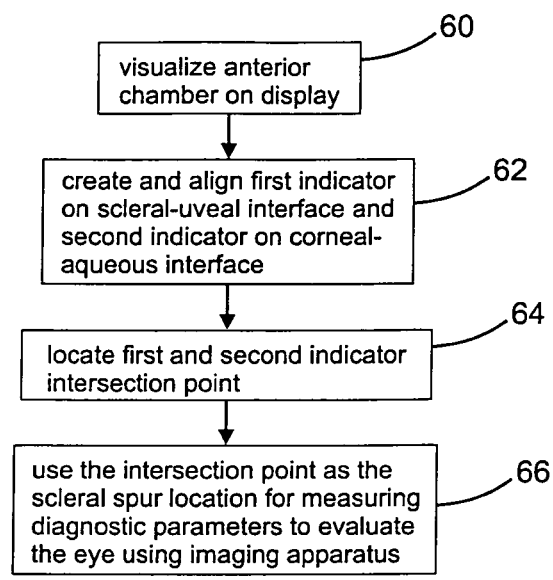
FIG. 9 is a flowchart illustrating method and means embodiments of the present invention.

Some embodiments of the invention include methods which may be accomplished by software for use with computerized imaging apparatus 50 capable of creating and manipulating an image of the anterior chamber of the eye, which may be visualized 60 on display 52, to enable the locating of scleral spur 20 and measurement of anterior chamber angle 30, angle opening distance 34, or other evaluations and measurements, as illustrated by flowchart on FIG. 9. For example, the computerized imaging apparatus 50 can comprise ultrasonic biomicroscopy apparatus, optical coherence tomography, etc. The software includes functions for creating 62 first indicator 54 aligned with scleral-uveal interface 42 on the image and second curvilinear indicator 56 aligned with corneal-aqueous interface 44 on the image, locating 64 intersection point 58 of first indicator 54 and second curvilinear indicator 56, and using 66 intersection point 58 to measure at least one geometric feature of the anterior chamber of the eye.

Figure 10:
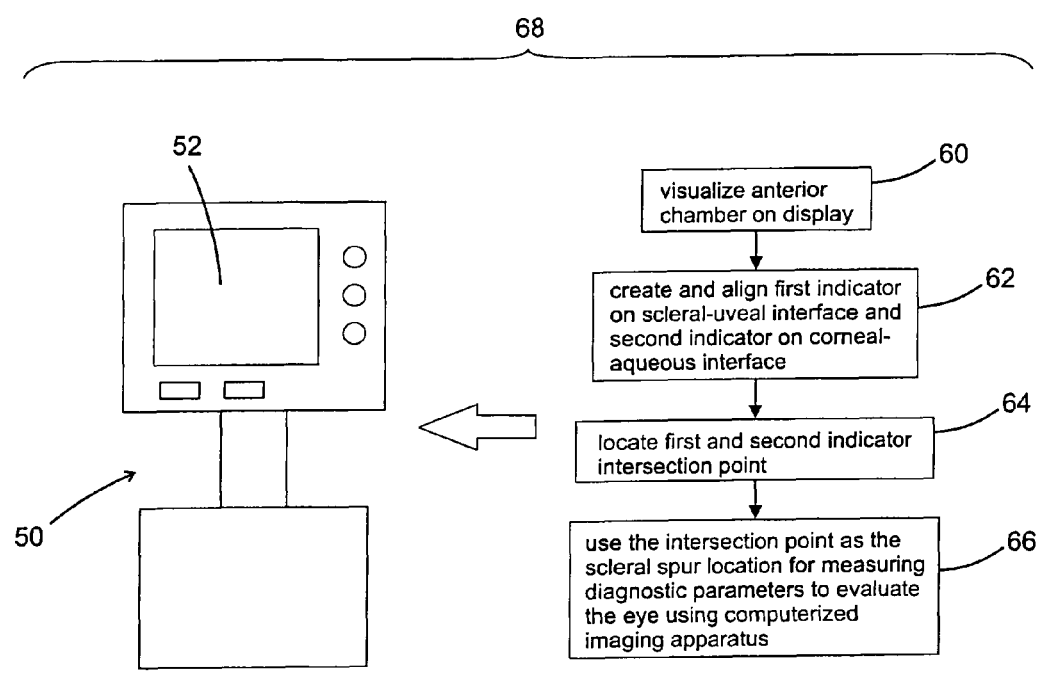
FIG. 10 illustrates a system comprising computerized imaging apparatus and means for locating the scleral spur according to the present invention.

Some embodiments of the invention include system 68 comprising computerized imaging apparatus 50 capable of creating and manipulating an image of the anterior chamber of the eye and visualizing 60 the image on display 52, and means for image processing on computerized imaging apparatus 50, the means for image processing enabling the locating of scleral spur 20 and measurement of anterior chamber angle 30, angle opening distance 34, or other evaluations and measurements, as illustrated on FIG. 10. The means for image processing includes functions for creating 62 first indicator 54 aligned with scleral-uveal interface 42 on the image and second curvilinear indicator 56 aligned with corneal-aqueous interface 44 on the image, locating 64 intersection point 58 of first indicator 54 and second curvilinear indicator 56, and using 66 intersection point 58 to measure at least one geometric feature of the anterior chamber of the eye. The image of the anterior chamber of the eye, first indicator 54 and second curvilinear indicator 56, intersection point 58, and other measurements and indicators, in any combination, may be displayed on display 52, to facilitate diagnosis or therapy of the eye. In some embodiments, the means for image processing can comprise software running on computerized imaging apparatus 50. In other embodiments, the image and indicators and measurements are calculated by software, but are not necessarily displayed so that they are graphically visible to the user.

Figure 11:
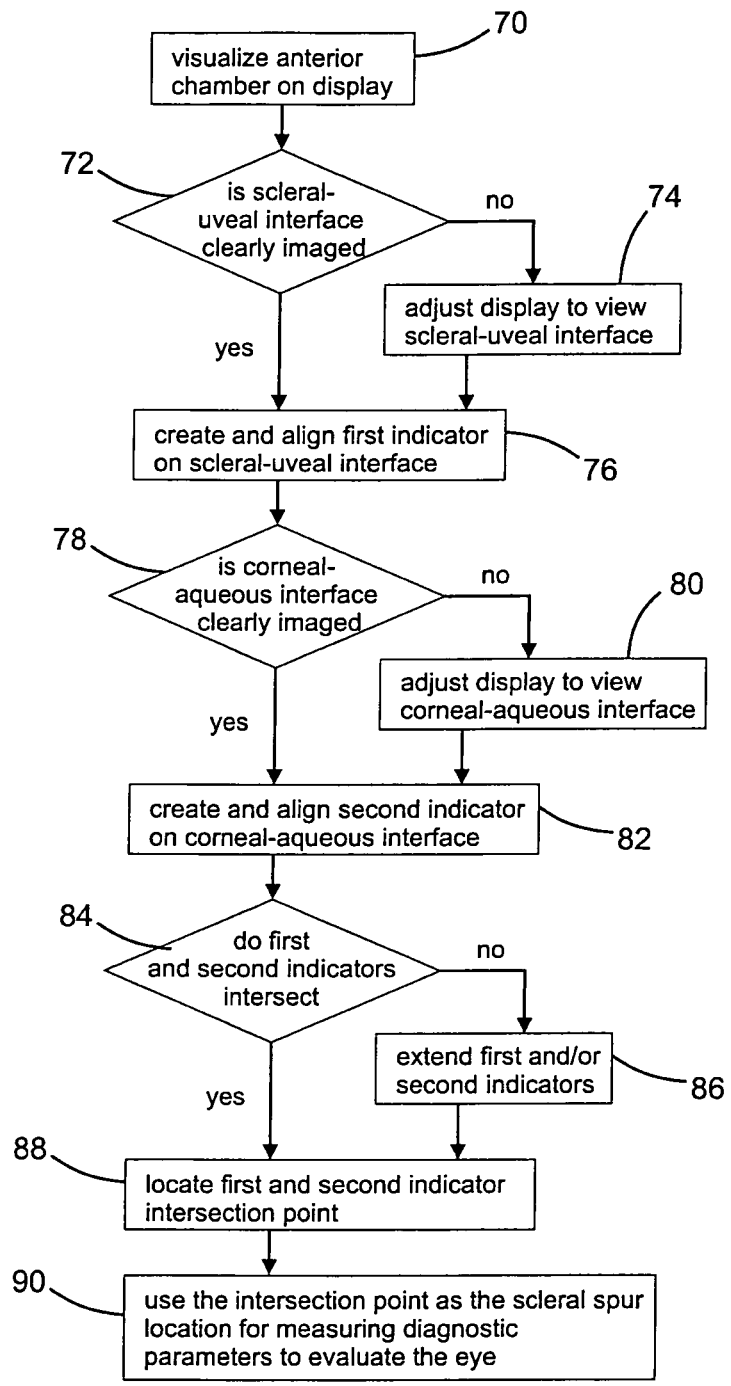
FIG. 11 is a flowchart illustrating more enhanced method and means embodiments of the present invention.

Some embodiments of the invention include more enhanced methods and/or means for image processing for use with computerized imaging apparatus 50 capable of creating and manipulating an image of the anterior chamber of the eye and visualizing 70 the image on display 52, to enable the locating of scleral spur 20 and measurement of anterior chamber angle 30, angle opening distance 34, or other evaluations and measurements, as illustrated by flowchart on FIG. 11. For example, computerized imaging apparatus 50 can comprise ultrasonic biomicroscopy apparatus, optical coherence tomography, etc. The means for image processing includes functions for determining 72 whether scleral-uveal interface 42 is adequately visualized, adjusting 74 the contrast, brightness, intensity, color, or other attributes of the image or display 52 if necessary to detect scleral-uveal interface 42, creating 76 first indicator 54 and aligning it with the scleral-uveal interface 42 on the image, determining 78 whether corneal-aqueous interface 44 is adequately visualized, adjusting 80 the contrast, brightness, intensity, color, or other attributes of the image or display 52 if necessary to detect corneal-aqueous interface 44, creating 82 second curvilinear indicator 56 and aligning it with inner corneal-aqueous interface 44 on the image, determining 84 whether first indicator 54 and second curvilinear indicator 56 intersect, extending 86 first indicator 54 and/or second curvilinear indicator 56 if necessary until they do intersect, locating 88 intersection point 58 of first indicator 54 and second curvilinear indicator 56, and using 90 intersection point 58 as the location of scleral spur 20 to measure at least one geometric feature of the anterior chamber of the eye.

Figure 12:
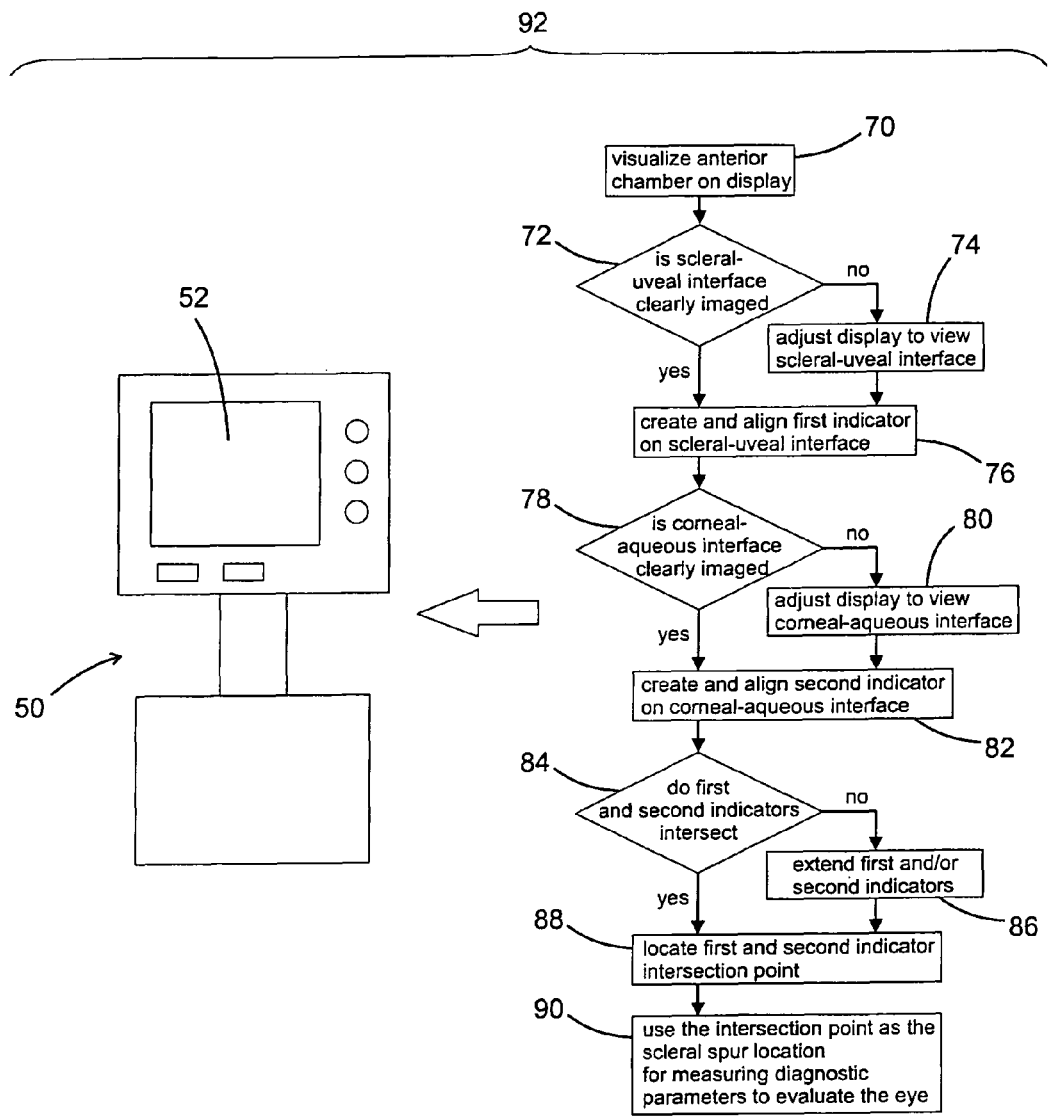
FIG. 12 illustrates a system comprising computerized imaging apparatus and more enhanced means for locating the scleral spur according to the present invention.

Some embodiments of the invention include system 92 comprising computerized imaging apparatus 50 capable of creating and manipulating an image of the anterior chamber/scleral-uveal interface of the eye and visualizing 70 the image on display 52, and more enhanced means for image processing on computerized imaging apparatus 50, the more enhanced means for image processing enabling the locating of scleral spur 20 and measurement of anterior chamber angle 30, angle opening distance 34, or other evaluations and measurements, as illustrated on FIG. 12. The more enhanced means for image processing includes functions for determining 72 whether scleral-uveal interface 42 is adequately visualized adjusting 74 the contrast, brightness, intensity, color, or other attributes of the image or display 52 if necessary to detect scleral-uveal interface 42, creating 76 first indicator 54 and aligning it with the scleral-uveal interface 42 on the image, determining 78 whether corneal-aqueous interface 44 is adequately visualized, adjusting 80 the contrast, brightness, intensity, color, or other attributes of the image or display 52 if necessary to detect corneal-aqueous interface 44, creating 82 second curvilinear indicator 56 and aligning it with corneal-aqueous 44 interface on the image, determining 84 whether first indicator 54 and second curvilinear indicator 56 intersect, extending 86 first indicator 54 and/or second curvilinear indicator 56 if necessary until they do intersect, locating 88 intersection point 58 of first indicator 54 and second curvilinear indicator 56, and using 90 intersection point 58 as the location of scleral spur 20 to measure at least one geometric feature of the anterior chamber of the eye. Any of these functions can be performed automatically, or using input from the user to activate or adjust the image or the positions of first indicator 54 and/or second curvilinear indicator 56 or intersection point 58. The image of the anterior chamber of the eye, first indicator 54, second curvilinear indicator 56, intersection point 58, and other measurements and indicators, in any combination, may be displayed on display 52, to facilitate diagnosis or therapy of the eye. In some embodiments, the more enhanced means for image processing can comprise more enhanced software.

In other embodiments, the image and indicators and measurements are calculated by software, but are not necessarily displayed so that they are graphically visible to the user. For example, image analysis functions and a best-fit line or curve generator can be used to create first indicator 54 and second curvilinear indicator 56, which can be displayed on display 52. The user can accept the displayed shapes and positions of first indicator 54 and second curvilinear indicator 56, or manually adjust them if needed. Alternatively, the software can perform all these manipulations, use intersection point 58 as the calculated location of scleral spur 20, utilize image analysis to calculate the anterior chamber angle 30 or angle opening distance 34 or other useful diagnostic parameter, and simply display the result for the user. A yes/no or go/no-go type indicator, graphical or text diagnostic description, or other indicator, can be used to inform the user of the results, or the quality of or confidence in the calculated results. Color, intensity, and indicator shapes can be used on display 52 to indicate or enhance various features and parameters detected or calculated and thereby to aid the user, such as an indicator arrow and removal of the two determinant lines for a cleaner/simpler display.

Various aspects and features of the illustrative embodiments, or various steps in the methods, means, or functions, can be combined, or performed in different orders, to achieve the desired utility in enhancing diagnosis or therapy of the eye.

Various modifications can be made to the present invention without departing from the apparent scope thereof.

METHODOLOGY TO IDENTIFY THE SCLERAL SPUR PARTS LIST 10 scleral tissue
12 uveal tissue
14 cornea
16 iris
18 aqueous humor
20 scleral spur
22 location (position)
24 location (position)
26 location (position)
30 anterior chamber angle
32 angle measurement distance
34 angle opening distance.
36 position
38 position
40 position
42 scleral-uveal interface
44 corneal-aqueous interface
50 computerized imaging apparatus
52 display
54 first indicator
56 second curvilinear indicator
58 intersection point
60 visualize
62 create
64 locate
66 use
68 system
70 visualize
72 determine
74 adjust
76 create
78 determine
80 adjust
82 create
84 determine
86 extend
88 locate
90 use
92 system It is claimed:
1. A method of locating the scleral spur including the steps of:
  a. providing computerized imaging apparatus for imaging the anterior chamber of the eye including several millimeters of adjacent sclera;
  b. creating an image of the anterior chamber of the eye including several millimeters of adjacent sclera;
  c. creating a first indicator aligned with the scleral-uveal interface on the image of the anterior chamber of the eye, said indicator can be a line or any form, shape or color following the scleral-uveal interface;
  d. creating a second indicator aligned with the corneal-aqueous interface on the image of the anterior chamber of the eye, said indicator can be curvilinear or any form, shape or color following the corneal-aqueous interface;
e. locating the intersection point of the first indicator and the second indicator; and,
f. using the intersection point of the first indicator and the second indicator as the location of the scleral spur for measurements of the anterior chamber of the eye.

2. The method of claim 1, further comprising the steps of:
a. determining whether the scleral-uveal interface is adequately imaged to align said first indicator;
b. adjusting the image as necessary to allow the first indicator to be aligned with the scleral-uveal interface;
c. determining whether the corneal-aqueous interface is adequately imaged to align said second indicator;
d. adjusting the image as necessary to allow the second indicator to be aligned with the corneal-aqueous interface;
e. determining whether the first indicator and the second indicator intersect; and,
f. extending the first indicator and the second indicator as necessary to locate the intersection point of the first indicator and the second indicator.

3. The method of claim 1, wherein the computerized imaging apparatus is selected from the group comprising ultrasonic biomicroscopy (UBM) and optical coherence tomography (OCT).

4. A method for locating the scleral spur comprising:
a. obtaining an image of the anterior chamber of the eye and several millimeters of sclera using computerized imaging apparatus;
b. providing additional computing apparatus for image processing of an image of the anterior chamber of the eye;
c. using the additional computing apparatus, locating the scleral-uveal interface on the image of the anterior chamber of the eye;
d. using the additional computing apparatus, creating a first indicator aligned with the scleral-uveal interface on the image of the anterior chamber of the eye;
e. using the additional computing apparatus, locating the corneal-aqueous interface on the image of the anterior chamber of the eye;
f. using the additional computing apparatus, creating a second curvilinear indicator aligned with the corneal-aqueous interface on the image of the anterior chamber of the eye;
g. in the additional computing apparatus, locating the intersection point of the first indicator and the second curvilinear indicator; and,
h. using the intersection point of the first indicator and the second curvilinear indicator as the location of the scleral spur for measurements of the anterior chamber of the eye.

5. The method of claim 3, further comprising the steps of:
a. determining whether the scleral-uveal interface is adequately imaged to align said first indicator;
b. adjusting the image as necessary to allow the first indicator to be aligned with the scleral-uveal interface;
c. determining whether the corneal-aqueous interface is adequately imaged to align said second curvilinear indicator;
d. adjusting the image as necessary to allow the second curvilinear indicator to be aligned with the corneal-aqueous interface;
e. determining the first indicator and the second curvilinear indicator intersection; and,
f. extending the first indicator and the second curvilinear indicator as necessary to locate the intersection point of the first indicator and the second curvilinear indicator.

6. The method of claim 4, wherein the computerized imaging apparatus is selected from the group comprising ultrasonic biomicroscopy (UBM) and optical coherence tomography (OCT).

7. A system for locating the scleral spur for the evaluation of the anterior chamber of the eye, comprising:
computerized imaging apparatus for forming an image of the anterior chamber of the eye as well as surrounding tissues of the eye including the uveal tissue, the scleral tissue, the cornea, the iris, and the aqueous humor;
said computerized imaging apparatus comprising first means for generating a first linear indicator upon said image of said anterior chamber of the eye which is aligned with a scleral-uveal interface upon said image of said anterior chamber of the eye;
said computerized imaging apparatus further comprising a second means for generating a second curvilinear indicator upon said image of said anterior chamber of the eye which is aligned with a corneal-aqueous interface upon said image of said anterior chamber of the eye;
said computerized imaging apparatus further comprising a third means for locating the intersection point of said first and second indicators; and
said computerized imaging apparatus further comprising a fourth means for using said intersection point of said first and second indicators as the location of the scleral spur so as to enable desired measurements of the anterior chamber of the eye relative to said scleral spur.

8. The system as set forth in claim 7, wherein:
said computerized imaging apparatus further comprises a fifth means for determining whether said scleral-uveal interface is adequately delineated so as to permit said first indicator to be aligned with said scleral-uveal interface, and for likewise determining whether said corneal-aqueous interface is adequately delineated so as to permit said second indicator to be aligned with said corneal-aqueous interface; and
said computerized imaging apparatus further comprises a sixth means for adjusting said images of said scleral-uveal and said corneal-aqueous interfaces as necessary so as to ensure that said first and second indicators are properly aligned with said scleral-uveal and said corneal-aqueous interfaces.

9. The system as set forth in claim 8, wherein:
said computerized imaging apparatus further comprises a seventh means for determining whether said first and second indicators intersect so as to accurately define said scleral spur, and for extending said first and second indicators, as necessary, so that said first and second indicators do in fact intersect and thereby define said scleral spur.

10. The system as set forth in claim 7, wherein:
said computerized imaging apparatus is selected from the group comprising ultrasonic biomicroscopy (UBM) and optical coherence tomography (OCT).

* * * * *